(12) United States Patent
Bailey

(10) Patent No.: US 8,979,820 B2
(45) Date of Patent: Mar. 17, 2015

(54) METHOD AND APPARATUS FOR IMPROVING THE APPEARANCE OF NAILS AFFECTED BY ONYCHOMYCOSIS THROUGH THE TOPICAL APPLICATION OF AN AQUEOUS SOLUTION CONTAINING BORIC ACID AND CAMPHOR OR OTHER TERPENES

(76) Inventor: Cynthia S. Bailey, Sebastopol, CA (US)

( * ) Notice: Subject to any disclaimer, the term of this patent is extended or adjusted under 35 U.S.C. 154(b) by 0 days.

(21) Appl. No.: 13/546,984

(22) Filed: Jul. 11, 2012

(65) Prior Publication Data

US 2012/0277693 A1    Nov. 1, 2012

Related U.S. Application Data

(63) Continuation-in-part of application No. 12/901,456, filed on Oct. 8, 2010, now abandoned.

(60) Provisional application No. 61/250,453, filed on Oct. 9, 2009.

(51) Int. Cl.
*A61M 31/00* (2006.01)
*A61B 17/54* (2006.01)
*A61K 9/00* (2006.01)
*A61K 31/137* (2006.01)
*A61K 31/17* (2006.01)
*A61K 31/27* (2006.01)
*A61K 31/4174* (2006.01)
*A61K 31/60* (2006.01)
*A61K 33/22* (2006.01)
(Continued)

(52) U.S. Cl.
CPC .......... *A61B 17/54* (2013.01); *A45D 29/00* (2013.01); *A61K 9/0014* (2013.01); *A61K 31/137* (2013.01); *A61K 31/17* (2013.01); *A61K 31/27* (2013.01); *A61K 31/4174* (2013.01); *A61K 31/60* (2013.01); *A61K 33/22* (2013.01); *A61K 9/08* (2013.01); *A61K 8/35* (2013.01); *A61Q 3/00* (2013.01); *A61K 8/19* (2013.01)
USPC ......................................... 604/518

(58) Field of Classification Search
USPC ........... 132/73, 73.5, 74.5, 75, 313; 15/167.3; 607/81–87, 94; 4/545, 574.1, 622; 424/659, 705; 514/588, 576
See application file for complete search history.

(56) References Cited

U.S. PATENT DOCUMENTS 2,061,142 A * 11/1936 Denocenzo ................. 4/622
3,510,554 A * 5/1970 Balsiger .................... 514/777
(Continued)

OTHER PUBLICATIONS

Larimore, M.D., Walter L, et al. Diary from a Week in Practice, Family Physician's Notebook, American Family Physician, vol. 49, No. 8, Jun. 1994; pp. 1767-1768.
(Continued)

*Primary Examiner* — Aarti B Berdichevsky
(74) *Attorney, Agent, or Firm* — Craig M. Stainbrook; Stainbrook & Stainbrook, LLP

(57) ABSTRACT

A method of treating onychomycosis and improving nail appearance for persons suffering onychomycosis, including preparing an aqueous solution containing between 0.3% and 28% (3 g/L or 0.049 mole/L and 280 g/L or 4.53 mole/L) boric acid and between 0.1% and 11% (1g/L or 0.0066 mole/L and 110 g/L or 0.072 mole/L) camphor or other terpene, and applying the solution to the affected nails for a period of time between a few seconds up to 30 minutes at least once per day every day for a sufficiently long period of time for the condition to appreciably improve or to resolve.

3 Claims, 14 Drawing Sheets

(51) Int. Cl.
  *A61K 9/08* (2006.01)
  *A61K 8/35* (2006.01)
  *A61Q 3/00* (2006.01)
  *A61K 8/19* (2006.01)
  *A45D 29/00* (2006.01)

(56) References Cited

U.S. PATENT DOCUMENTS

| | | | |
|---|---|---|---|
| 5,840,283 A * | 11/1998 | Sorenson et al. | 424/61 |
| 6,664,292 B2 | 12/2003 | Bogart | |
| 6,676,953 B2 | 1/2004 | Hexamer | |
| 6,846,837 B2 | 1/2005 | Maibach et al. | |
| 6,878,365 B2 | 4/2005 | Brehove | |
| 6,921,529 B2 | 7/2005 | Maley | |
| 6,951,847 B2 | 10/2005 | Gibson et al. | |
| 6,960,201 B2 | 11/2005 | Cumbie | |
| 7,582,621 B2 | 9/2009 | Baker et al. | |
| 7,767,657 B2 | 8/2010 | Baker et al. | |
| 7,816,344 B2 | 10/2010 | Baker et al. | |
| 2006/0207017 A1 * | 9/2006 | Lev et al. | 4/622 |
| 2008/0038375 A1 * | 2/2008 | Park | 424/715 |

OTHER PUBLICATIONS

Larimore, M.D., Walter L., et al. Diary from a Week in Practice, American Family Physician, Aug. 15, 2000.

Author Unknown. Page from Family Physician's Notebook (Aug. 1994,) American Family Physian, vol. 50, No. 2.

Larimore, M.D., Walter L., et al. Diary from a Week in Practice, American Family Physician, Nov. 1, 1999, vol. 60, No. 7, The American Family Physician Web archives.

* cited by examiner

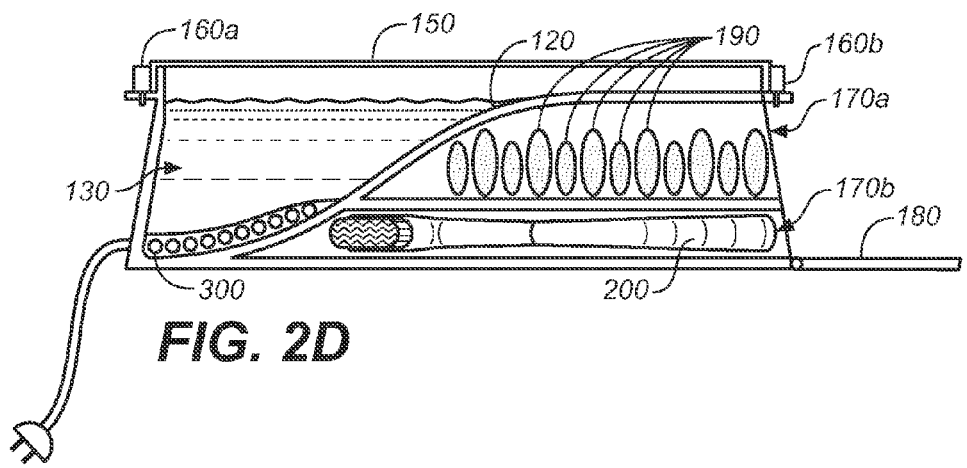
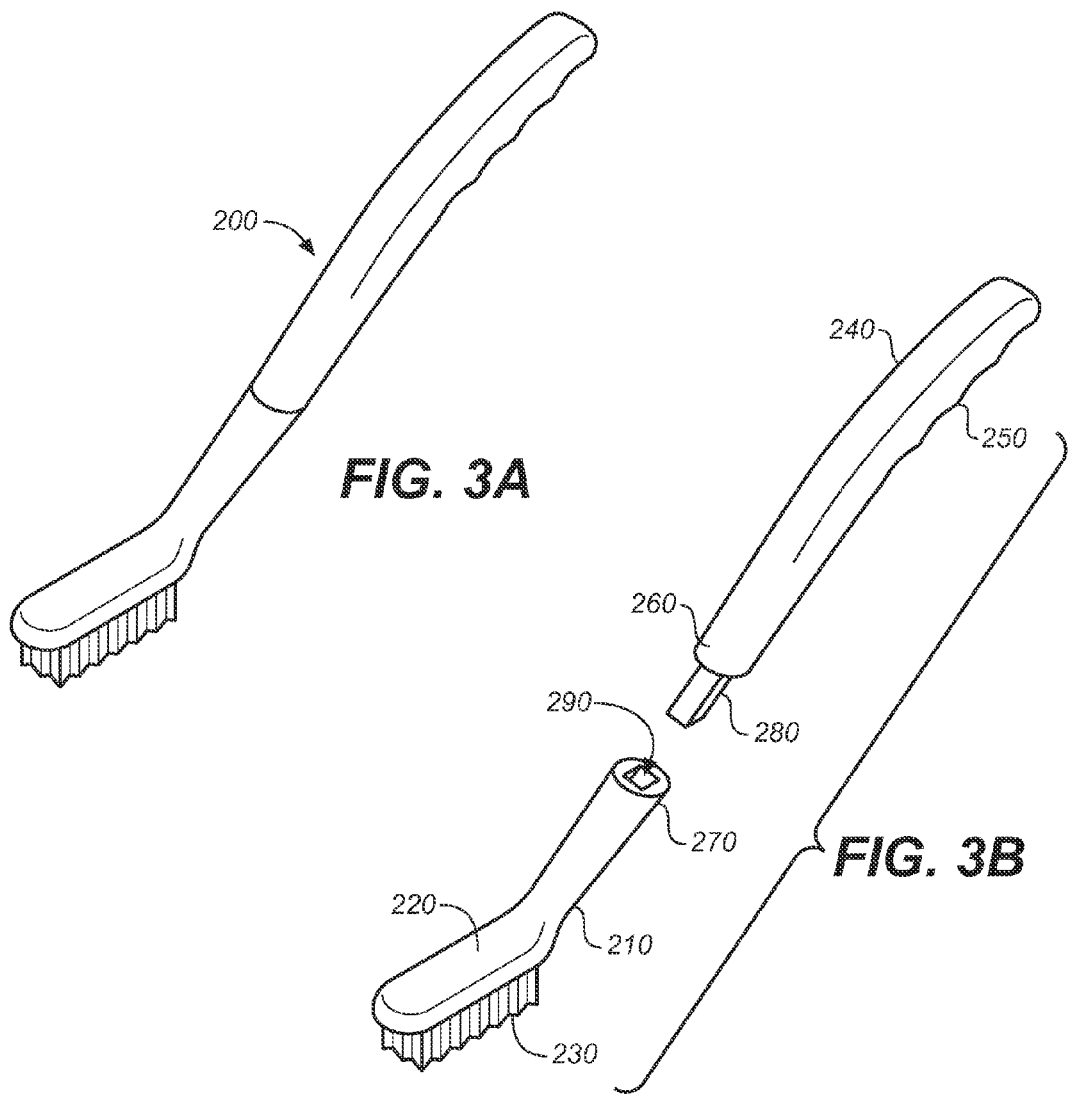

FIG. 4

| FIG. 4A |
| FIG. 4B |
| FIG. 4C |

FIG. 4A

Toe Nail Study Participants

| PT ID | START DATE | DATES SEEN | PICTURE | ASSESSMENT |
|---|---|---|---|---|
| BC8834 | 5/15/08 | 5/15/08 | BC 8834 05.15.08 | |
| | | 10/8/08 | BC 8834 10.08.08 | |
| BP925 | 6/3/08 | 6/3/08 | BP 925 06.03.08 | |
| | | 9/30/08 | BP 925 09.30.08 | |
| CA10838 | 4/16/08 | 4/16/08 | CA 10838 04.16.08 | |
| | | 8/12/08 | CA 10838 08.12.08 | |
| | | 10/17/08 | CA 10838 10.17.08 | |
| CB9199 | 8/20/08 | 8/20/08 | CB 9199 8.20.08 | |
| | | 10/17/08 | CB 9199 10.17.08 | |
| CP4746 | 3/6/08 | 3/6/08 | CP 4746 03.06.08 | |
| | | 5/20/08 | CP 4746 05.20.08 | |
| | | 6/25/08 | CP 4746 06.25.08 | |
| | | 8/28/08 | CP 4746 08.28.08 | |
| CV10942 | 11/16/07 | 11/16/07 | CV10942 11.16.07 | DROPPED OUT due to non-compliance |
| | | 3/17/08 | CV10942 3.17.08 | |
| DC7387 | 2/14/08 | 2/14/08 | DC 7387 02.14.08 | |
| | | 4/10/08 | DC 7387 04.10.08 | |
| | | 6/5/08 | DC 7387 06.05.08 | |

FIG. 4B

| | | | |
|---|---|---|---|
| FC10057 | 2/15/08 | 8/6/08 | DC 7387 08.06.08 | |
| | | 9/22/08 | DC 7387 09.22.08 | DROPPED OUT due to non-compliance |
| | | 2/15/08 | FC10057 02.15.08 | |
| | | 3/30/08 | FC10057 03.30.08 | |
| GR9872 | 11/7/07 | 11/7/07 | GR9872 11.07.07 | DROPPED OUT due to unrelated health problems |
| | | 3/6/08 | GR9877 03.06.08 | |
| JD950 | 6/10/08 | 6/10/08 | JD 950 06.10.08 | |
| | | 10/10/08 | JD 950 10.10.08 | |
| JI11244 | 11/29/07 | 11/29/07 | JI 11244 11.29.07 | |
| | | 3/27/08 | JI 11277 03.27.08 | DROPPED OUT due to non-compliance |
| JM | 2/5/08 | 2/5/08 | JM 02.05.08 | |
| | | 10/6/08 | JM 10.06.08 | |
| JT143 | 11/16/07 | 11/16/07 | JT 143 11.16.07 | |
| | | 3/7/08 | JT 143 03.07.07 | |
| | | 6/3/08 | JT 143 06.03.08 | |
| | | 9/8/08 | JT 143 09.08.08 | |
| | | 10/7/08 | JT 143 10.07.08 | |
| KC7594 | 10/27/06 | 10/27/06 | NOT ELECTRONIC | ** PRIOR TO DIGITAL PHOTOS |
| | | 12/15/06 | NOT ELECTRONIC | ** PRIOR TO DIGITAL PHOTOS |
| | | 1/25/08 | KC 7594 01.25.08 | |
| | | 3/28/08 | KC 7594 03.28.08 | |
| KK3102 | 3/21/08 | 3/21/08 | KK 3102 03.21.08 | |
| | | 3/28/08 | KK 3102 03.28.08 | |
| | | 7/21/08 | KK 3102 07.21.08R | |
| | | 7/21/08 | KK 3102 07.21.08L | |
| | | 10/20/08 | KK 3102 10.20.08 | |
| LC2837 | 5/1/07 | 5/1/07 | LC 2837 05.01.07 | |
| | | 11/2/07 | LC 2837 11.02.07 | |

| LZ10536 | 6/6/08 | 6/6/08 | LZ 10536 06.06.08 |
|---|---|---|---|
| | | 10/10/08 | LZ 10536 10.10.08 |
| MB9537 | 3/14/08 | 3/14/08 | MB 9537 03.14.08 |
| | | 6/24/08 | MB 9537 06.24.08 |
| | | 9/12/08 | MB 9537 09.12.08 |
| | | 10/13/08 | MB 9537 13.13.08 |
| ML3099 | 3/18/08 | 3/18/08 | ML 3099 03.18.08 |
| | | 7/22/08 | ML 3099 07.22.08 |
| | | 10/3/08 | ML 3099 10.03.08 |
| MR6849 | 11/7/07 | 11/7/07 | MR 6849 11.07.07 |
| | | 3/6/08 | MR 6849 03.06.08 |
| | | 10/6/08 | MR 6849 10.06.08 |
| MR8960 | 3/27/08 | 3/27/08 | MR 8960 03.27.08 |
| | | 9/25/08 | MR 8960 09.28.08 |
| TN6054 | 6/12/08 | 6/12/08 | TN 6054 06.12.08 |
| | | 10/14/08 | TN 6054 10.14.08 |
| WS7098 | 2/7/08 | 2/7/08 | WS 7098 02.07.08 |
| | | 8/11/08 | WS 7098 08.11.08 |

| FIG. 5A | FIG. 5B | FIG. 5C |
|---------|---------|---------|
| FIG. 5D | FIG. 5E | FIG. 5F |

FIG. 5A

Toe Nail Study Results

| Patient ID Code | Treatment Duration | Treatment Interruption | Patient Age | Number of Years with Probable Fungus | Culture Results | Prior Treatments N=None T=Topical L=Lamisil | Nail Accessed | Area of Involvement Before | Proximity of Disease to Matrix Before |
|---|---|---|---|---|---|---|---|---|---|
| Dramatic Improvement | | | | | | | | | |
| CP4746 | 6months | no | 55 | 30 | + | T | RG | 2 | 4 |
| KC7594 | 17months | no | 62 | 5 | + | L/T | RG | 5 | 5 |
| LC2837 | 6months | no | 76 | unk | n/a | unk | RG | 2 | 3 |
| MB9537 | 7months | no | 88 | many | + | N | RG | 4 | 3 |
| WS7098 | 6months | no | 63 | 2 | + | N | L2 | 3 | 5 |
| Severity Index Average | | | | | | | | | |
| Group Average Age | | | 68.8 | | | | | | |
| Significantly Improved | | | | | | | | | |
| BP925 | 4months | no | 54 | 10 | + | N | LG | 4 | 5 |
| CA10838 | 6months | no | 67 | 10 | + | N | LG | 3 | 4 |
| JD950 | 4months | no | 59 | 20 | + | T | RG | 5 | 5 |
| LZ10536 | 4months | no | 76 | 2 | + | T | RG | 5 | 4 |
| ML3099 | 7months | yes | 59 | 8 | + | L | RG | 2 | 5 |
| MR8960 | 6months | no | 62 | 3 | + | N | L2 | 3 | 2 |
| TN6054 | 4months | no | 61 | many | + | L/T | RG | 4 | 3 |

FIG. 5B

Toe Nail Study Results

| Dermatophytoma or Subungual Hyperkeratosis Before | Severity Rating Before | Area of Involvement After | Proximity of Disease to Matrix After | Dermatophytoma or Subungual Hyperkeratosis After | Severity Rating After | Patient's Comments |
|---|---|---|---|---|---|---|
| Dramatic Improvement |||||||
| 0 | 8 | 1 | 0 | 0 | 0 | only thing that ever worked |
| 10 | 35 | 3 | 3 | 0 | 9 | Perfect looking |
| 0 | 6 | 0 | 0 | 0 | 0 | |
| 10 | 22 | 1 | 1 | 0 | 1 | much improved |
| 10 | 25 | 1 | 0 | 0 | 0 | dramatic change |
| | 19.2 | | | | 2 | |
| Significantly Improved |||||||
| 10 | 30 | 2 | 3 | 0 | 6 | absolutely better |
| 0 | 12 | 2 | 2 | 0 | 4 | it's working |
| 10 | 35 | 4 | 3 | 0 | 12 | it's working |
| 0 | 20 | 3 | 3 | 0 | 9 | improving |
| 10 | 20 | 2 | 4 | 0 | 8 | better |
| 10 | 16 | 1 | 1 | 0 | 1 | improving |
| 0 | 12 | 2 | 2 | 0 | 4 | improved, hoped would be gone |

FIG. 5C

Toe Nail Study Results

| Patient ID Code | Notes on Severity Index Rating |
|---|---|
| | Dramatic Improvement |
| CP4746 | |
| KC7594 | |
| LC2837 | |
| MB9537 | |
| WS7098 | |
| | Significantly Improved |
| BP925 | |
| CA10838 | RG more dramatic but pre photo angled and can't rate area |
| JD950 | 4 months treatment and approx 4mm new growth |
| LZ10536 | |
| ML3099 | poor prognosis dermatophytoma improving |
| MR8960 | |
| TN6054 | |

| | | | | | | | | |
|---|---|---|---|---|---|---|---|---|
| Severity Index Average | | | | | | | | |
| Group Average Age | | 62.6 | | Subtle Improvement | | | | |
| JT143 | 11 months | 67 | many | + | L | LG | 3 | 5 |
| KK3102 | 7months | 63 | many | + | T | LG | 5 | 5 |
| MR6849 | 11months | 70 | 12 | + | T | LG | 5 | 5 |
| Severity Index Average | | | | | | | | |
| Group Average Age | | 66.7 | | No Improvement | | | | |
| BC8834 | 5 months | 57 | many | + | N | RG | 3 | 3 |
| CB9199 | 2months | 82 | 2 | - | T | LG | 3 | 2 |
| DC7387 | 7 months | 67 | 1.50 | + | N | LG | 3 | 4 |
| JM | 8 months | 54 | 30 | + | T | L2 | 5 | 5 |
| Severity Index Average | | | | | | | | |
| Group Average Age | | 65 | | | | | | |

| Onychomycosis Severity Index Key |
|---|
| 0 is Cured |
| 1-5 is Mild Disease |
| 6-15 is Moderate Disease |
| 16-35 is Severe Disease |

*FIG. 5D*

|  |  |  |  |  |  |  |
|---|---|---|---|---|---|---|
| | | | | | 20.71 | |
| | | | | | | 6.286 |
| Subtle Improvement | | | | | | |
| 10 | | 25 | 3 | 4 | 12 | 24 | thinks improving |
| 10 | | 35 | 5 | 4 | 10 | 30 | helping more than anything ever has, improving |
| 10 | | 35 | 4 | 4 | 10 | 26 | thinks improving, stopped using for months |
| | | 31.67 | | | | 26.67 |
| No Improvement | | | | | | |
| 0 | | 9 | 3 | 3 | 0 | 9 | no change seen |
| 10 | | 16 | 3 | 2 | 10 | 16 | thinks is improving |
| 0 | | 12 | 3 | 5 | 10 | 25 | getting worse |
| 10 | | 35 | 5 | 5 | 10 | 35 | very noncompliant |
| | | 18 | | | | 21.25 |

FIG. 5E

| Subtle Improvement | |
|---|---|
| JT143 | |
| KK3102 | very difficult disease to impact |
| MR6849 | very difficult disease to impact |
| No Improvement | |
| BC8834 | |
| CB9199 | only used for 2 months before study closed |
| DC7387 | |
| JM | |

*FIG. 5F*

METHOD AND APPARATUS FOR IMPROVING THE APPEARANCE OF NAILS AFFECTED BY ONYCHOMYCOSIS THROUGH THE TOPICAL APPLICATION OF AN AQUEOUS SOLUTION CONTAINING BORIC ACID AND CAMPHOR OR OTHER TERPENES

CROSS REFERENCES TO RELATED APPLICATIONS

The present application is a continuation-in-part of U.S. Utility patent application Ser. No. 12/901,456, filed Oct. 8, 2010 (Oct. 8, 2010), which in turn claims the benefit of the filing date of U.S. Provisional Patent Application Ser. No. 61/250,453, filed Oct. 9, 2009 (Oct. 9, 2009), published as US Pat. Appl. Pub. No. 2011/0083692, and incorporated in its entirety by reference herein.

STATEMENT REGARDING FEDERALLY SPONSORED RESEARCH OR DEVELOPMENT

Not applicable.

NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

SEQUENCE LISTING

Not applicable.

BACKGROUND OF THE INVENTION

1. Field of the Invention

The present invention relates generally to compositions and methods of using such compositions for the treatment of skin conditions, and more particularly to a method of using a dermatological composition comprising an aqueous solution containing boric acid and camphor or other terpenes for the treatment of onychomycosis.

2. Background Discussion

Onychomycosis is a fungal infection of the fingernails or toenails. The condition is difficult to cure. Onychomycosis occurs when dermatophytes (specifically, tinea unguium fungi) infect one or more nails. In the early stage of the infection, the area around the base and the sides of the nail may become red and irritated. If the fungus is allowed to spread deeper into the bed of the nail, it may cause discomfort, itching, and pain around the cuticles, and even bleeding and detachment of the cuticles. The nail may become discolored, perhaps yellow-green or dark yellow-brown, and white spots occasionally appear in the nail. Eventually, the nail thickens and develops abnormal grooves, lines, and broken and crumbling edges. Saprophytic molds, yeast and bacteria often co-infect or colonize the nail unit infected with dermatophytes to worsen the nail deformity and confound treatment in onychomycosis. This heterogeity of infecting microorganisms often explains treatment failure in that these different classes of microorganisms require differing antimicrobial agents to eradicate.

Tinea unguium fungi and co-infecting microorganisms thrive in warm, moist environments, so fungal nail infections generally develop under nails continually exposed to warm, moist environments, e.g., swimming pools, showers, and sweaty shoes. Predictably, infection in toenails is significantly more common than infection in fingernails, due to the fact that toenails are covered with shoes—creating the very kind of warm, moist environment in which fungi thrive. Relatively low blood circulation and slow nail growth rates may also be a contributing factor.

Nail fungal infections can be painful and may cause permanent nail damage. They can pose a serious health risk for people with diabetes or compromised immune systems.

Unfortunately, nail fungus can be difficult to treat, and recurrence is common. Over-the-counter antifungal nail creams, ointments and solutions are largely ineffective. Prescription medications are generally much more effective. The better known medications available by prescription include itraconazole (Sporanox); fluconazole (Diflucan); and terbinafine (Lamisil). However, these medications require an aggressive six to twelve week drug regimen or repeat courses of oral ingestion and may require four to twelve months to entirely eliminate an infection. Additionally, a typical twelve week course of treatment can cost upwards of $700 or more and still has only a 50-70% chance of curing the condition. Furthermore, these antifungal drugs may cause serious side effects, including liver damage, and monitoring of liver function by a physician is imperative. Adverse drug interactions also pose a serious risk for people on other systemic medicines.

For a relatively mild fungal nail infection, some doctors may prescribe an antifungal lacquer, such as ciclopirox (Penlac). This topical medication is painted onto the infected nails and surrounding tissue daily, so that several layers of lacquer build up over the course of a week. After one week, the seven layers are wiped off using an alcohol swab, and this is followed by another series of fresh applications. Studies show that this treatment is effective in less than 10 percent of patients using it.

If the nail infection is severe or extremely painful, a doctor may even recommend removing the nail during topical treatment. While a new nail will eventually grow in its place, the discomfort is not inconsiderable, and protection from injury and other invasive organisms is lost for a length of time.

Onychomycosis can be controlled and the appearance of the nails improved by applying undecylenic acid, which is approved by the FDA and is sold under a number of brand names, such as Blis-To-Sol Powder, Breezee Mist Foot Powder, Caldesene Powder, Cruex, Desenex, Fungoid AF, Pedi-Pro, and Protectol. This, however, is not a cure.

Numerous other methods have been proposed for the treatment of fungal nail infections. Patents showing compositions and their use in such treatments include U.S. Pat. No. 6,986,896, to Bhagwat, et al, which discloses a method of treating fungal conditions and onychomycosis through the administration of a safe and effective amount of urea in a topical formulation to an affected area on the skin or around a nail of a patient in need of treatment.

U.S. Pat. No. 6,960,201, to Cumbie, teaches a method of treating microbial infections occurring just below the skin and nails consisting of the application of electromagnetic radiation to an infected area of skin or nails for a time and at a proximity and intensity sufficient to render the microbes substantially inactivated and incapable of reproducing.

U.S. Pat. No. 6,951,847, to Gibson, et al, teaches a method of treating fungal and yeast infections using lupeol or solvates, hydrates, or clathrates.

U.S. Pat. No. 6,921,529, to Maley, shows a method of treating onychomychosis wherein a hydrogel is supersaturated with an antimycotic agent and supported on a backing The assembly is placed over an infected nail for an extended period of time. The antimycotic agent diffuses through the nail to the underlying infection. The antimycotic agent can be used alone or in conjunction with other active agents or carriers. Alternative therapeutic agents mentioned in the patent include iodine, DMSO, azole derivatives, undecylenic acid, tea tree oil, salicylic acid, urea, and any other recognized antimycotic agent.

U.S. Pat. No. 6,878,365, to Brehove, discloses a topical application for treating onychomycosis using a composition that comprises, as an active ingredient, at least one species selected from the group consisting of 2,2'-(alkyldioxy)bis-(alkyl-1,3,2-dioxaborinane) and 2,2'-oxybis(alkyl-1,3,2-dioxaborinane). The composition comprises, as an active ingredient, at least one member selected from the group consisting of 2,2'-(1-methyltrimethylenedioxy)bis-(4-methyl-1,3,2-dioxaborinane) and 2,2'-oxybis(4,4,6-trimethyl-1,3,2-dioxaborinane).

U.S. Pat. No. 6,846,837, to Maibach, et al, teaches a method and topical pharmaceutical formulations for the treatment of onychomycosis using a pharmacologically active antifungal agent, plus a pharmaceutically acceptable base in a formulation having a pH of 7.5 to about 13.0, preferably about 8.0 to 11.5, and most preferably about 8.5 to 10.5. The antifungal agent is selected from the group consisting of amorolfine, ciclopirox olamine, flucytosine, griseofulvin, haloprogrin, potassium iodide, sodium pyrithione, undecylenic acid, bifonazole, butoconazole, clotrimazole, econazole, ketoconazole, miconazole, oxiconazole, sulconazole, itraconazole, fluconazole, terconazole, naftifine, amphotericin B, nystatin, benzoic acid, salicylic acid, propionic acid, and caprylic acid.

U.S. Pat. No. 6,676,953, to Hexamer, discloses an antifungal composition for the treatment of fungal infections in human nails comprising an aqueous solution of a wetting agent such as alcohol and a source of fluoride ions sufficient to establish a pH ranging from about 2.8 to about 3.5 in the composition.

U.S. Pat. No. 6,664,292, to Bogart, teaches a method of treating pathological conditions of the nail comprising topically applying an effective amount of an optionally substituted lower alcohol and an optionally substituted lower carboxylic acid.

The foregoing patents and prior art methods are illustrative and exemplary only and reflect the current state of the art of which the present inventor is aware. Reference to, and discussion of, these patents is intended to aid in discharging Applicant's acknowledged duty of candor in disclosing information that may be relevant to the examination of prospective claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is a method and apparatus for treating nails affected by onychomycosis. The method improves the appearance of nails when an aqueous solution of boric acid and camphor or other terpenes is applied to the affected nails in a systematic and routine manner that limits cutaneous exposure to this otherwise potentially toxic or irritating, but effective treatment solution.

The difficulty with topical treatment of onychomycosis has historically been due to the resistance of the nail plate and the nail unit structure to absorb topically applied active ingredients. It is known that the nail plate absorbs more water than any other keratin structure on the human body, such as skin or hair. Nails are composed of hydrophobic lipid layers alternating with hydrophilic keratin layers. Successful topical treatment of onychomycosis has been hindered by nail penetration difficulties into these two structural nail layers. The art discussed in the background section did not present a solution to this problem.

The present invention employs a unique synergistic composition including boric acid and camphor or other terpenes in aqueous solution. The efficacy of the combination is believed to be based on the presence of both an antimicrobial hydrophobic and a hydrophilic small molecule active present in an aqueous solution that is readily taken up into the layered nail plate structure. In addition, both compounds have proven efficacy against a broad range of pertinent microorganisms including bacteria, yeast, fungi and molds. Topical exposure of the skin to high concentrations of these compounds is also potentially toxic and/or irritating and thus the soaking tray design allows treatment of the nail while limiting the potential for percutaneous exposure.

Boric acid, which is hydrophilic, is readily carried into the nail plate as the plate absorbs water. Once in the nail structure, it exerts an antimicrobial effect on the infecting microorganisms. It is also present in excess in the solution and can easily enter the numerous cracks, crevices and onychogryphotic spaces of the excessive keratin debris characteristic of onychomycosis, thus treating the saprophytic molds, yeasts, and bacteria that reside in these spaces and that co-infect the nail unit.

Camphor and other terpenes are lipophilic and known to readily penetrate the lipid layers of keratin skin-related structures such as the skin under and around the nail unit. They are a proven skin penetration enhancer and proven antimicrobial agents. The synergistic duel action of both hydrophilic and hydrophobic antimicrobial actives, both of which readily and uniquely penetrate the nail unit, is believed to be why the inventive treatment solution is uniquely efficacious for the topical treatment of onychomycosis. The method of treatment is designed to create the optimal nail state for maximal absorption in a practical application setting for home use.

In addition, the synergism of boric acid and camphor or other terpenes in aqueous solution allows for the successful topical treatment of onychomycosis at lower concentrations of these two potentially toxic active ingredients. It is believed that at the treatment concentrations used these actives do not react chemically, but instead both enter the disparate hydrophilic and lipid/hydrophobic elements of the nail unit intact to treat the infecting organisms in their optimal antimicrobial chemical forms.

Boric acid and camphor or other terpenes together penetrate the otherwise penetration-resistant components of the nail unit. Each component appears to enhance the limited solubility of its companion component into the aqueous solution. Optimal treatment ranges for these ingredients, designed to preserve the unique antimicrobial properties of both are 0.1% (1 g/L or 0.0066 mole/L) to 11% (110 g/L or 0.072 mole/L) for camphor and from 0.3 (3 g/L or 0.049 mole/L) to supersaturated (which is believed to be approximately 28 percent (280 g/L or 4.53 mole/L) in boiling water) for boric acid.

The invention also includes an apparatus for applying the synergistic combination in solution. The apparatus is a treatment kit that includes premeasured boric acid ($H_3BO_3$) and camphor ($C_{10}H_{16}O$), each preferably provided in a plurality of packets for mixing a solution either in a bottle of predetermined size or in the soaking tray included in the inventive apparatus. After preparing the solution, it is poured into a soaking tray (if not prepared in the tray itself). The tray has a fluid reservoir or basin in which to soak toenails. The tray also includes an angled footrest or ramp that descends down into the fluid reservoir so that the user can limit exposure to the toes and toenails only, sparing contact of the entire foot to the potentially toxic and/or irritating treatment solution. A specially designed nail brush is provided to ergonomically debride loose keratin onychogryphotic material and other debris, enhancing solution penetration and minimizing soaking time to assist in minimizing unwanted cutaneous exposure. An effective treatment regimen entails exposing the affected nails daily for a period several second to several minutes for a long enough period of time to either resolve the condition entirely or to achieve discernible improvement in the appearance of the affected nails.

The foregoing summary broadly sets out the more important features of the present invention so that the detailed description that follows may be better understood, and so that the present contributions to the art may be better appreciated. There are additional features of the invention that will be described in the detailed description of the preferred embodiments of the invention which will form the subject matter of the claims appended hereto.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2D is a cross-sectional side view in elevation showing an alternative embodiment of the soak tray including an integrated heating unit;

FIG. 3A and 3B are upper perspective views showing the angled brush employed in the method of the present invention;

FIGS. 4A-4C collectively comprise a table showing the study group engaged in a clinical study conducted to determine the efficacy of the inventive method and composition to improve the appearance of onychomycotic toenails and/or toenails infected with dermatophytes and other fungal and yeast organisms; and FIGS. 5A-5F collectively comprise a table showing the response summary, including a pre- and post-treatment disease severity index rating.

DETAILED DESCRIPTION OF THE INVENTION

Figure 1A:
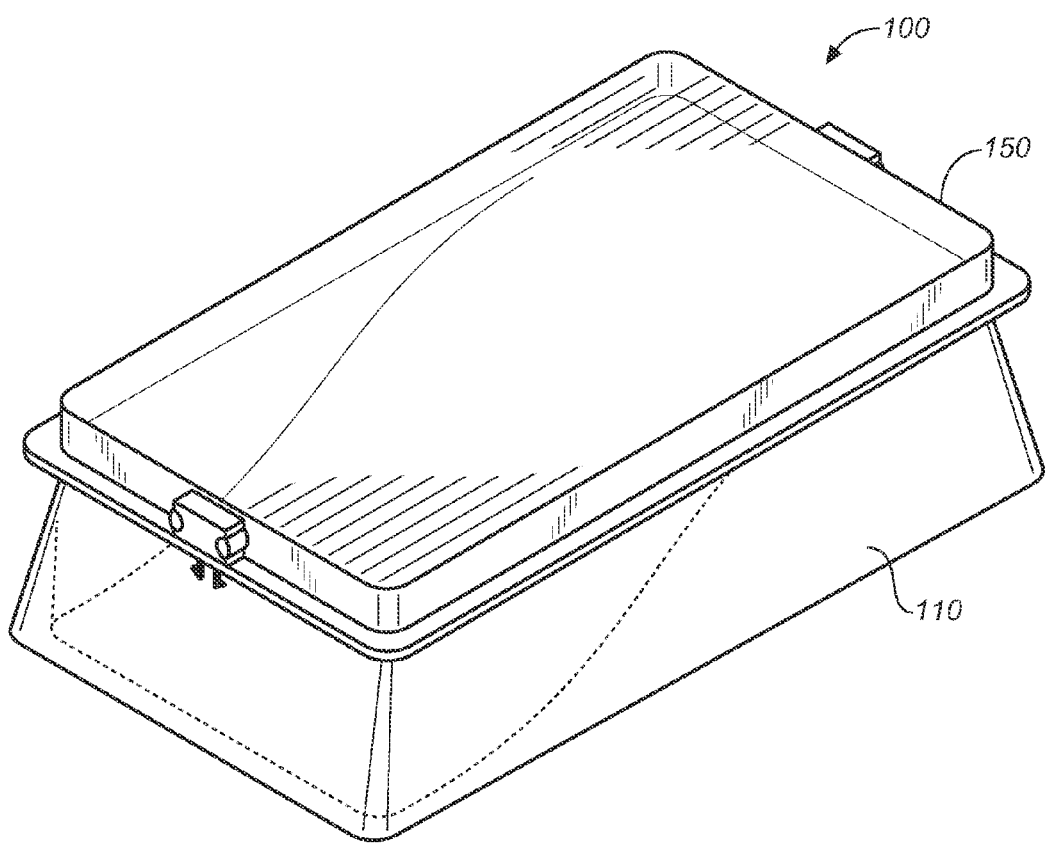
FIG. 1A is an upper front perspective view of the soaking tray of the present invention, shown with a tamper proof lid installed.
Figure 1B:
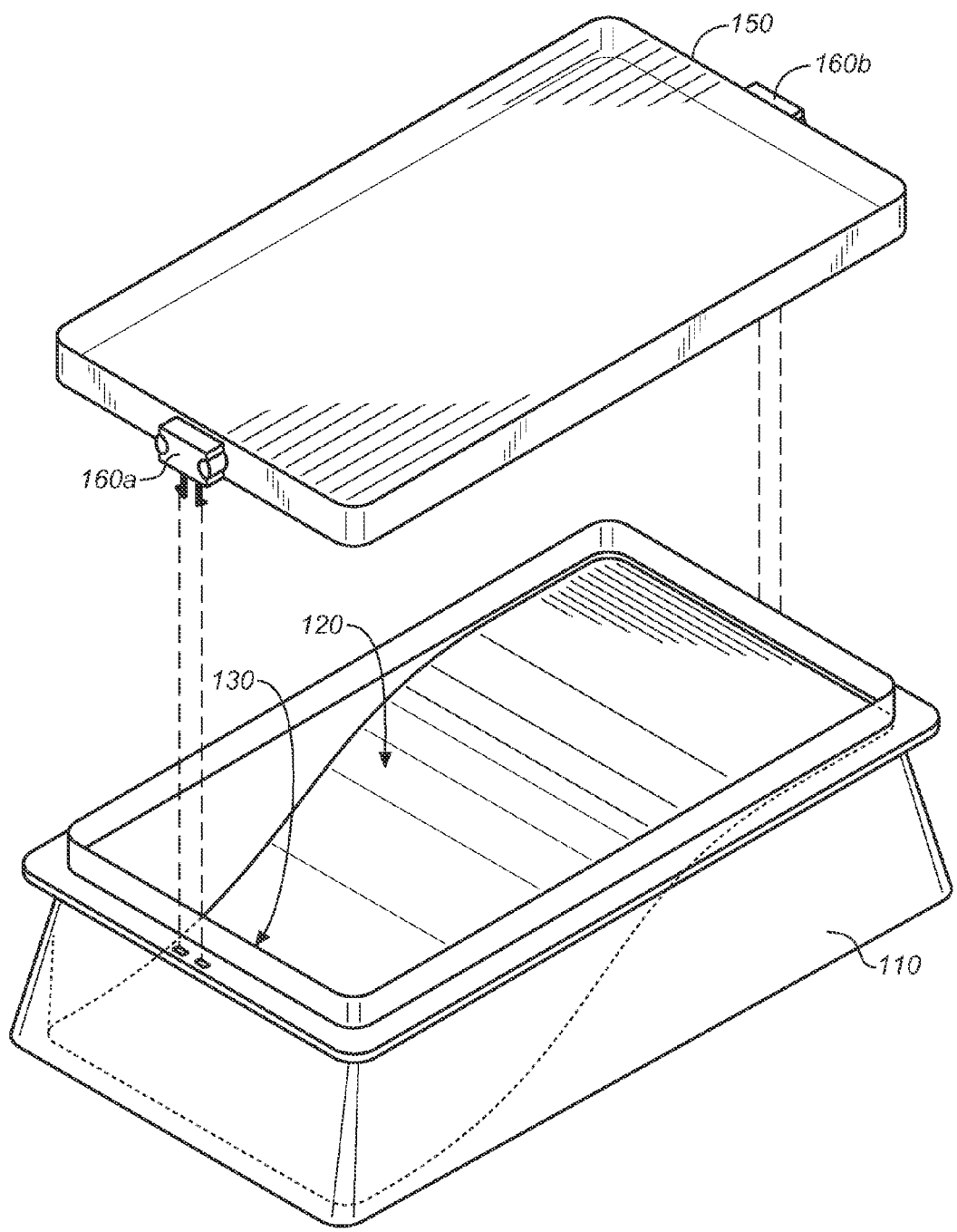
FIG. 1B shows the apparatus of FIG. 1A with the lid removed.

The present invention is a method and apparatus for regularly and systematically treating onychomycosis using a boric acid solution comprising 0.3% to 28% boric acid and 0.1% to 11% camphor or other terpenes dissolved in warm water. Additional ingredients may include a keratolytic agent, such as urea or salicylic acid; an antifungal agent, such as clotrimazole or tolnaftate; a botanical or fragrance such as eucalyptus oil, menthol, melaleuca oil, or other essential oils. Additional therapeutic ingredients might include iodine, ethyl alcohol, and/or sulfur. As yet the mechanism of the treatment is not entirely understood and a determination of whether the treatment comprises a cure for onychomycosis has not yet been made. However, clearly discernible improvements in nail appearance result from disciplined application of the treatment and at times these improvements result in a total resolution of the onychomycotic nail deformity and are sustained indefinitely after discontinuation of the treatment application. Accordingly, as used herein, the term "treatment" does not signify a proven mycological cure but only an effective program for improving nail appearance for persons suffering from onychomycosis.

The inventive apparatus is a treatment kit that includes packets of boric acid ($H_3BO_3$), and camphor or other terpene, preferably provided in a plurality of pre-measured packets for mixing a solution either in a bottle of predetermined size or in the soaking tray included in the inventive apparatus. In preparing the treatment solution, the user simply pours a recommended amount of powder into a bottle, sealable bag, or in the soaking tray described below, covers the container with a lid, and the solution is shaken until a solution of desired saturation is produced. If a supersaturated solution is used, some powder will invariably remain undissolved as the sought after solution is supersaturated.

The mixed solution may be used repeatedly for up to one week. However, a boric acid solution may be poisonous when ingested. Further, the United States Food and Drug Administration limits the use of boric acid in personal care products to 5% and camphor to 11%. Boric acid has been reported to cause seizures after ingestion or occluded powder exposure to the diaper area of infants. Camphor is known to be irritating in high concentrations. Thus, the FDA has placed solution exposure limits to control the potential levels of these agents in or on the human body. However, these known antimicrobial water soluble agents have been found effective for the treatment of onychomycosis of the toenails.

A specialized soaking tray was therefore designed to limit percutaneous exposure and absorption of a highly concentrated onychomycosis treatment solution. The soaking tray was designed to enable safe nail treatment based on the selective absorption of the nails and relative impermeability of the toe skin to water. Toenails selectively absorb more water than the other keratin structures of the human body, including skin, making aqueous treatment solutions advantageous for selective absorption into the nail unit. Toes conversely constitute only 1% of the body surface area of skin and are relatively impermeable owning to the thickness of toe skin To utilize safe but highly concentrated aqueous boric acid and camphor for nail treatment the soaking tray was designed to submerge only the toes and toenails in the treatment solution. The soaking tray inclines the foot in an ergonomic fashion that can be utilized by all but the most inflexible foot. The incline places the toes into the shallow treatment well because articulation at the metatarsophalangeal joint allows the foot to bend and the toes to submerge into the solution. A brief toe and toenail soak in the highly concentrated aqueous solution results in negligible percutaneous absorption of the ingredients; by submerging only the impermeable toes in the solution, percutaneous absorption of the active ingredients into the body is limited and the risk for toxicity negligible thus allowing treatment with highly concentrated solutions. The soaking tray design offers utility for other treatment solutions for nail disorders where there is a similar need to limit cutaneous exposure.

Figure 2A:
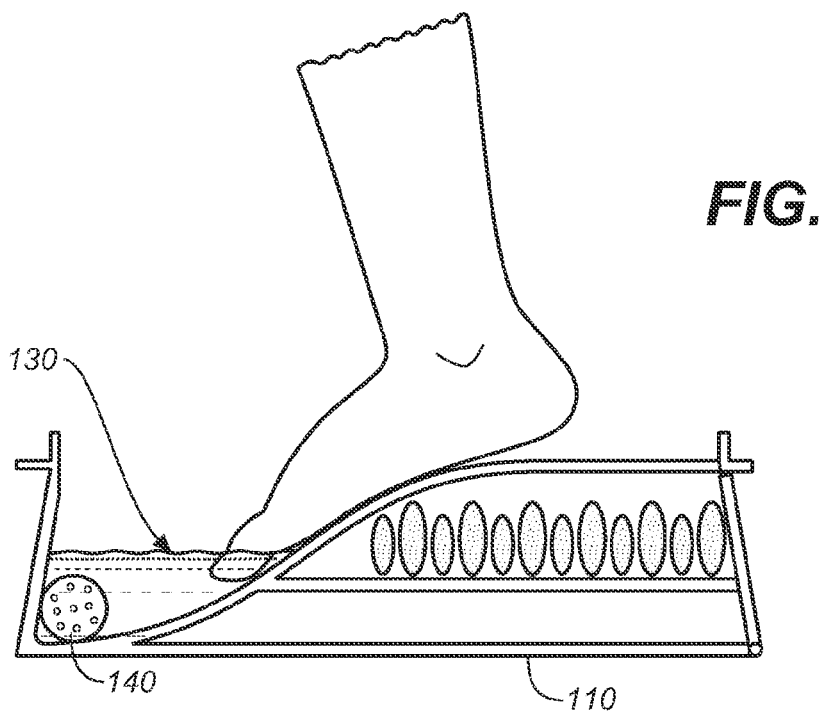
FIGS. 2A and 2B are each cross-sectional side views in elevation showing the soaking tray or soaking tray containing the treatment solution in a fluid reservoir and showing the solution used by a person suffering from onychomycosis with solution exposure limited to the toes and nails by articulation at the metatarsophalangeal joint of the foot.
Figure 2B:
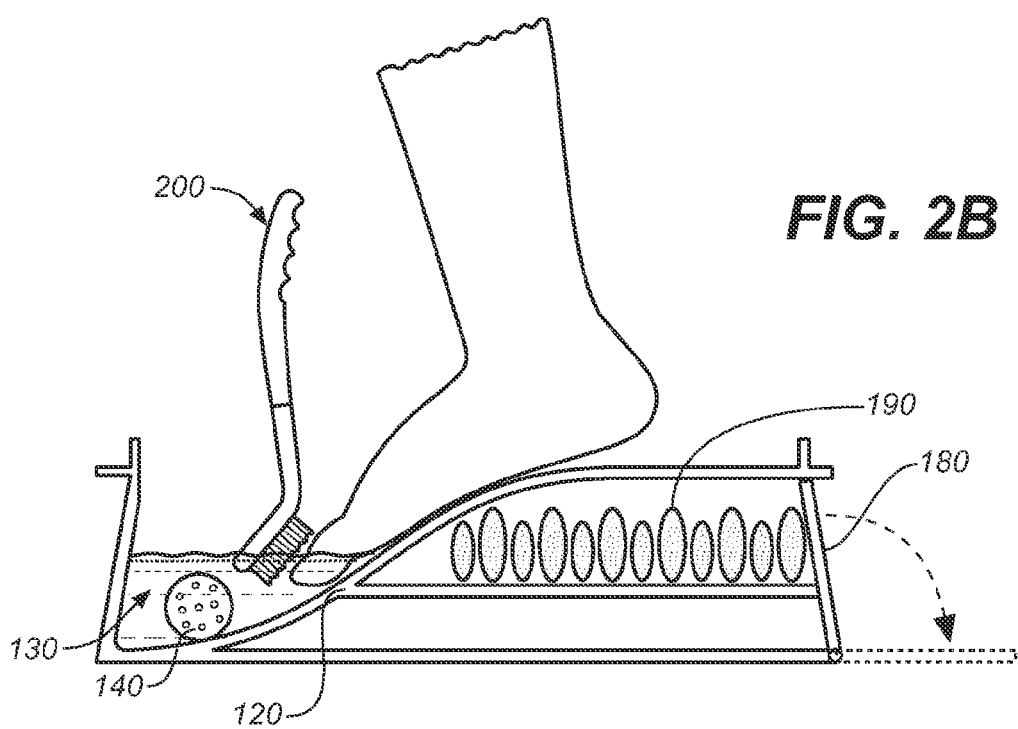
Figure 2C:
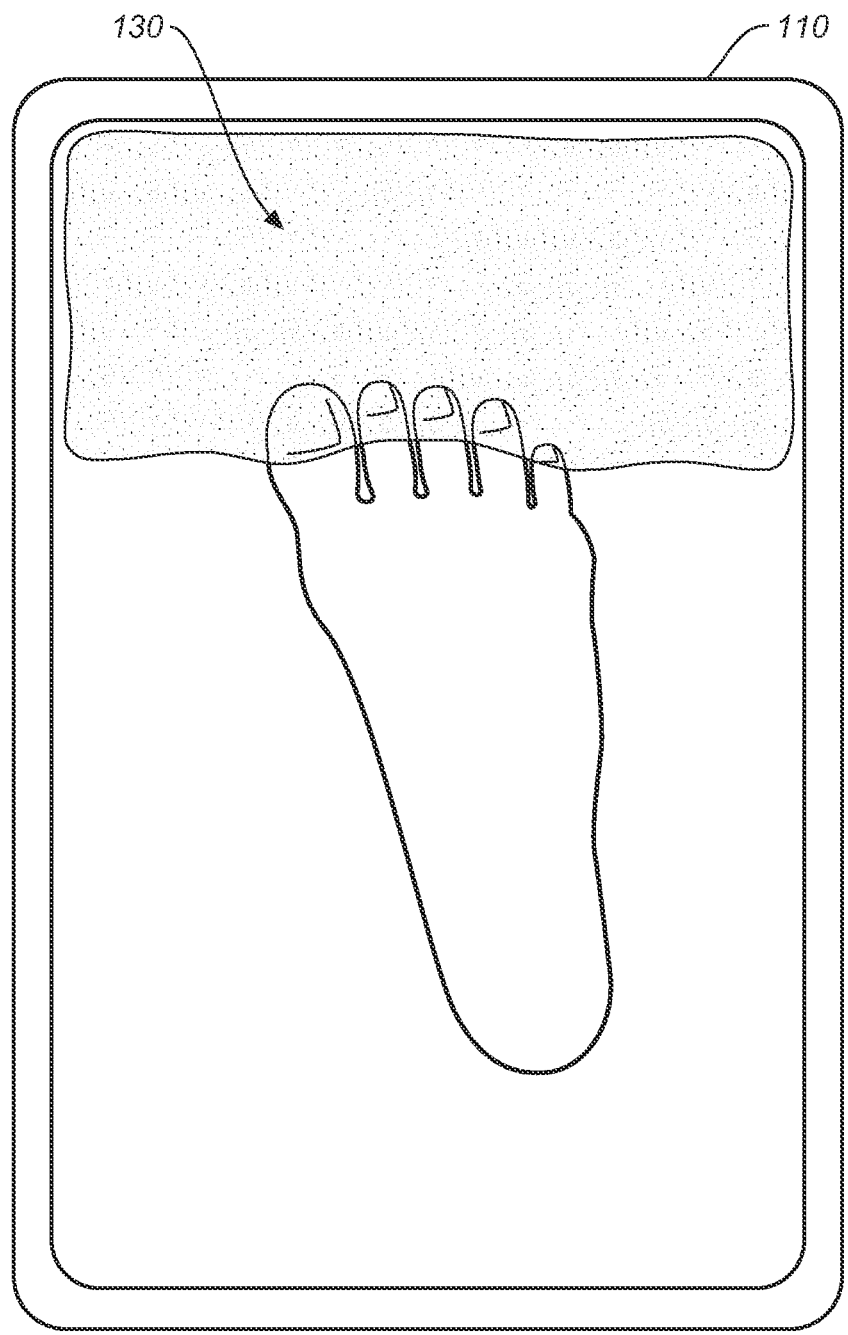
FIG. 2C is a top plan view showing how the toes are soaked using the soaking tray.

The apparatus that achieves treatment efficacy and also addresses the above-described safety objectives is shown in FIGS. 2A-2B, and includes a soaking tray 100 that provides a convenient basin in which to soak toenails, but which limits the exposure of the skin on the user's foot to that of the toes and toenails. This is due to the configuration of the soaking tray, which is a generally square or cuboid container base 110 having an angled footrest or interior ramp 120 that descends down to a small reservoir 130 into which only the forefoot or nail portion of the toes is submerged due to articulation at the metatarsophalangeal joint. A waffle ball 140 is provided to enhance the effectiveness of agitating the bottle or tray for mixing the solution and may be kept in the reservoir even during use.

Accordingly, however, to prevent accidental poisoning of animals and small children the soaking tray includes a tamper proof lid 150 having front and rear latches 160a, 160b that require conscious and coordinated handling to remove. The tray further includes one or two pockets 170a, 170b covered with a hinged door 180 operatively connected to rear latch that may be opened to store a plurality of packets 190 of boric acid and camphor or other terpene, as well as the nail brush described below.

Additionally, as shown in FIGS. 3A-3B, a specially designed nail brush 200 is also provided. This brush is fashioned generally in the shape of a toothbrush having an angled handle 210. The handle bends 220 immediately behind the bristle bed 230 at roughly a 45 degree angle and extends upwardly for a total length of approximately 8 inches. The uppermost portion of the handle 240 is provided with a ribbed grip 250 having indentations to conform to most finger types to facilitate easy handling. Moreover, the grip is divided into an upper handle 260 portion and a lower handle portion 270 that may be separated for easy storage and for product packaging. The halves may be assembled with snap fit male/female connection elements 280, 290. This elongated brush will enable elderly, obese, disabled, or otherwise incapacitated persons to scrub the nails while soaking in the soaking tray without having to bend over significantly. Furthermore, the brush will facilitate accurate painting of the nails with the treatment solution, thereby limiting unwanted cutaneous exposure.

In an alternative embodiment, FIG. 2D, soaking tray also includes electric heating coils or elements 300 either integrated into the interior ramp 120 or disposed in a compartment immediately below the ramp for effective heat transfer through the ramp to the boric acid and camphor or other terpene solution in the tray.

Returning now to the treatment process, once the solution is prepared, it is either poured into the soaking tray or the soaking tray lid is simply removed to expose the solution and to provide access to the ramp for resting the feet and immersing the toes in the solution.

Treatment Process: Patients treat their affected toenails every day for at least four months according to a therapeutically effective protocol. The following method steps comprise the recommended treatment procedure employing the inventive composition:

First—Nail Maintenance: The affected nails should be trimmed and maintained as short as possible during the treatment period. The surface of the nail should be filed with a nail file or buffed with an emery board to keep the nail plate as thin as possible. Nails may be professionally filed, or removed either surgically or chemically by a physician in preparation for the treatment.

Second—Surrounding Skin Treatment: The skin of the toes (or fingers, if treated) proximate the nails should be treated for fungal infection (tinea pedis/manus) using Lamasil (terbinafine hydrochloride) or clotrimazole cream twice a day for two months to ensure that no skin fungal infection exists prior to commencing treatment Skin adjacent to the nails must be entirely intact and free from any injury, blister, or other condition that would allow increased absorption of the potentially toxic and/or irritating ingredients through the skin Third—Preparing the Boric Acid and Camphor or Other Terpene Solution: After completing the second step, the boric acid and camphor or other terpene solution should be prepared to a strength of between 0.3% to 28% (or supersaturated) boric acid, and 0.1% to 11 percent camphor. If a supersaturated solution is used, the solution may be prepared by first preparing a saturated solution, i.e., one that contains the maximum amount of solutes that the water solvent will dissolve at room temperature and pressure, and thereafter heating the solution to dissolve and accept more solute. Any excess solute may be filtered out and the temperature then reduced.

Fourth—Treating the Nails: The affected nails are then soaked for only a few seconds to several minutes (up to 30 minutes) every day until the fungal infection is resolved. Nails should be dry and ideally not exposed to water for one hour prior to treatment and two hours after treatment. Nails soak up more water than hair or skin and the important element with this treatment is that the nails will soak up the medicated ingredients, bringing them in contact with the fungus and co-infecting microorganisms that are growing throughout the nail plate and in the outer layer of the skin underlying and adjacent to the plate. This will not happen if the nail is already significantly hydrated or if fresh water from bathing rinses out the medicated ingredients immediately after they have soaked into the nail. The angled brush is provided to scrub the nails while they are in the solution. The nails are then dried. This daily treatment must be done for many months because nails need to be treated until the fungal infected portion grows out. It takes about a year for a toenail to grow from the base of the cuticle to the end of the nail bed.

The soaking treatments should be continued an additional four months even after the condition has resolved. Further, treatment may be repeated as needed to maintain normal nails. During the course of treatment, the portion of the nail affected by fungus will slowly grow out to the end of the nail and will be replaced by a normal appearing nail. Nail fungal infections have a high relapse rate and future treatments may be necessary.

Optional use notes: Rather than providing heating elements in the soaking tray for heating the solution, the boric acid/camphor or other terpene solution and the soaking tray may be heated prior to use by placing the soaking tray on a heating pad or heating for several seconds in a microwave. Additionally, the solution may be saved and reused for up to one week by placing lid on soaking tray and storing at room temperature.

To facilitate healing and to prevent recurrence, it is recommended that the user take the following steps: (a) wear loose fitting shoes that breathe and absorbent cotton socks, or sandals; avoid occlusive shoes that do not breath while undergoing this treatment; (b) dust shoes daily with an antifungal powder such as Zeasorb AF; and (c) do not apply nail polish or ointments to the nail while undergoing this treatment as they will interfere with the absorption of the medicine into the nail plate.

From the foregoing it will be appreciated that boric acid and camphor have been found to be uniquely synergistic in the topical treatment of onychomycosis because they overcome nail penetration resistance that has made the topical treatment of nail fungus generally unsuccessful in the past. As earlier noted, it is believed that the synergistic efficacy derives from having both an antimicrobial hydrophobic and a hydrophilic small molecule present in an aqueous solution, which is therefore readily taken up into the layered nail plate structure.

Empirical Support and Studies: A clinical study was conducted to determine whether this novel toenail soak can improve the appearance of onychomycotic toenails and/or toenails infected with dermatophytes and other fungal and yeast organisms. The study patients were selected based on their personal interest. The design of the study was to demonstrate the feasibility of the treatment and prove or disprove the efficacy of the treatment. The study was not designed to prove mycologic cure, nor was it conducted using a control group, randomization of participants and blinding of the investigator.

Method: Patients were selected during the course of their physical exams or referred by patients in the medical practice of the present inventor. Prospective participants were excluded from the study if they had used an oral antifungal, or topical antifungal product on their toenails in the past 12 months. The initial study enrollment visit included a toenail fungal culture on DTM media, baseline toenail photographs, and instructions in oral and written form (see the patient instruction sheet included in U.S. Utility patent application Ser. No. 12/901,456, filed Oct. 8, 2010, Pub. No. US 2011/0083692). The patients were given the materials for treatment. Patients were instructed to return in 4 months and 6 months during which time photos were taken. Office exams scheduled for other purposes were also used to examine the toenails. Interested patients could continue treatment for up to 12 months. The study period was closed October 2008 at which time all participants in the treatment were given their final assessment regardless of treatment duration. Clinical assessment at the end of the treatment period was based on an assessment of the appearance of the involved toenails as seen in the photographs. Patients were assigned to one of several groups based on the degree of discernible improvement, i.e., no discernible improvement, subtle improvement, significant improvement, and dramatic improvement with near normal nail appearance.

Results: 23 patients were included in the study. 21 patients were enrolled from November 2007 to August 2008. Two (2) additional patients were included who used treatment before the study began and had sufficient documentation to be included in the study. The entire study group is listed in the table set out in FIGS. 4A-4C.

Four patients dropped out of the study after beginning treatment due to lack of interest or motivation and are not included in the analysis. There were no adverse events during the treatment.

Of the 19 participants who completed the treatment, four (4) had no change in the appearance of the nail (21%), three (3) had a subtle change in appearance (16%), seven (7) had significant improvement in the appearance of the nail (37%), and five (5) had dramatic improvement and near normal nail appearance (26%) The results are summarized in the table set out as FIGS. 5A-5F, which collectively comprise a spreadsheet including Severity Index Ratings of disease pre and post treatment. All participants except the 'no improvement' group experienced improvement in the severity of their onychomycotic nail deformity.

The groups with "significant" and "dramatic" improvement had "an improved appearance of the nail" and thus 63% of treatment participants fell into this category. 37% therefore had no change in the nail appearance during the treatment period.

The average age of the study participants was 65.4 years. There was no appreciable difference in age between the four response groups. FIGS. 5A-5F also lists the average ages, treatment duration, and percent of participants within each response group. Average treatment duration for the group as a whole was 6 months.

Discussion: Topical treatment for onychomycosis has historically been disappointing. It is a surprise that this new topical treatment method produced improvement in the appearance of onychomycotic toenails. Even more surprising was that this improvement in appearance occurred in an elderly population of participants. The elderly are considered a group with a poor prognosis for onychomycosis. The oldest patient in the study was 88 years old (MB9537). She had suffered nail fungus for many years, and despite this, she had near normal nail appearance after 7 months of treatment. The same is true for 76 year old LC2837 and 62 year old KC7594.

The results suggest that if nail appearance is going to respond favorably to this treatment, it does so promptly. If the nail is not going to respond, then continuing to use the treatment does not seem to alter the outcome. The average treatment duration of the participants was six (6) months. The group that improved (significant and dramatic) used the treatment for five months nine days (5.3) months. The treatment duration in the non-improved group (no change and subtle) was eight (8) months. Please note that this was calculated by removing a patient that was a late enrollee CB9188. This patient was only on the treatment for two months before the end of the study period, during which time he did not show an appreciable change in his nail photos, in spite of his assertion that he was improving. He was thus counted as a non-responder rather than being excluded from the study.

The participants' impressions of the treatment and their comments reflect the marketability of the product. CP4746 had toenail fungus for over 30 years and her nails improved to normal appearance after five (5) months. She had tried many topical remedies without response. Her pedicure technician had witnessed the process with her for many years and was also struck by the improvement. CP4746 said: "My nails were yellow, ridged, bumpy and thick for 30 years. My pedicurist is amazed . . . " People suffering nail fungus are disinclined to take oral medications because of the potential risks. KK3102, a subtle responder, said "the treatment is helping more than anything he ever used before including that expensive shellac." BP925, who had "significant" improvement in nail appearance following only four (4) months of treatment said "the nail is absolutely better." Lastly, all four of the participants who had used Lamasil without success felt that they were improving on the treatment.

In summary, the novel daily topical treatment of the present invention can improve the appearance of the onychomycotic nail. It works in the elderly, a group with a poor prognosis. In this patient group, a nonsystemic therapeutic alternative for improving the nail appearance has the advantage of avoiding medication drug interactions. It may also be a beneficial topical adjunct to systemic therapy in patients who want to use systemic antifungals.

An important advantage of the present invention is its ease of use. Ultimately, the boric acid and camphor or other terpene powders should be agitated and stored in a childproof bottle. A plastic dipping pan that fits all foot sizes and is inclined toward the toenails aids in the ease of use. Aggressive debridement of the nail by the patient correlated with treatment success and needs to be stressed in the instructions. The inventive method is an inexpensive, over-the-counter alternative to expensive pharmaceutical antifungals and ineffective OTC home remedies.

Oral antifungal treatments, such as Lamasil, are possibly the most effective treatment for nail onychomycosis, though firm conclusion will require further study. However, for people who do not wish to use a systemic antifungal therapy, the novel topical treatment disclosed herein affords improvement in the nail appearance.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

What is claimed as invention is:

1. A method of treating onychomycosis and improving nail appearance for persons suffering onychomycosis, comprising the steps of:
   (a) treating skin proximate the affected nails for fungal infection with a topical antifungal composition to ensure that no skin fungal infection exists prior to commencing treatment with the boric acid solution;
   (b) providing a soaking tray having a fluid reservoir and an angled footrest;
   (c) preparing an aqueous solution containing between 0.3% and 28% (3 g/L or 0.049 mole/L and 280 g/L or 4.53 mole/L) boric acid and between 0.1% and 11% (1 g/L or 0.0066 mole/L and 110 g/L or 0.072 mole/L) camphor;
   (d) pouring the boric acid and camphor containing solution into the soaking tray;
   (e) trimming, filing, and thinning the affected nails during the treatment period; and
   (f) soaking the affected nails for a period of time between a few seconds up to 30 minutes at least once per day every day until the infected portion of the nail grows out to the end of the nail and is replaced by a normal appearing nail.

2. The method of claim 1, further including the step of keeping the affected nails dry and not exposed to water for one hour prior to treatment and two hours after treatment.

3. The method of claim 1, further including the step of heating the boric acid and camphor solution before use.

* * * * *